(12) United States Patent
Amit

(10) Patent No.: US 8,323,107 B2
(45) Date of Patent: Dec. 4, 2012

(54) METHOD AND DEVICE FOR SCOREKEEPING WATCH

(75) Inventor: Rafi Amit, Atlit (IL)

(73) Assignee: Rafi Amit, Atlit (IL)

(*) Notice: Subject to any disclaimer, the term of this patent is extended or adjusted under 35 U.S.C. 154(b) by 90 days.

(21) Appl. No.: 13/047,807

(22) Filed: Mar. 15, 2011

(65) Prior Publication Data

US 2011/0230265 A1 Sep. 22, 2011

Related U.S. Application Data

(60) Provisional application No. 61/314,174, filed on Mar. 16, 2010.

(51) Int. Cl.
*G06F 17/00* (2006.01)
*G06F 19/00* (2011.01)
(52) U.S. Cl. .................... 463/35; 700/91; 700/92
(58) Field of Classification Search ............ 463/35, 463/39, 40, 42; 700/91, 92
See application file for complete search history.

(56) References Cited

U.S. PATENT DOCUMENTS

| | | | |
|---|---|---|---|
| 5,803,451 A * | 9/1998 | Kelly et al. | 273/118 R |
| 5,949,679 A * | 9/1999 | Born et al. | 700/91 |
| 6,634,548 B1 * | 10/2003 | Bowman | 235/1 B |
| 6,986,712 B1 * | 1/2006 | Ogawa | 463/42 |
| 7,611,410 B2 * | 11/2009 | Nakajima et al. | 463/29 |
| 2006/0034160 A1 * | 2/2006 | Berseth et al. | 368/223 |

* cited by examiner

*Primary Examiner* — Ronald Laneau
(74) *Attorney, Agent, or Firm* — Reches Patents

(57) ABSTRACT

A device for monitoring a first player, the device includes: a location unit; a score button; a score calculating unit arranged to: receive a first player score indication, transmit a first player score message to another device that is designed to trigger a first player score alert, determine whether to update a first player score value based on at least zero responses to the first player score message, and update the first player score value based on the determination; a feedback unit arranged to receive a second player score message about an intent of a second player to update a second player score value, generate a second player score alert, and transmit a first player response based on at least zero responses of the first player to the second player score alert; and a display for displaying the first player score value and at least one other player score value.

22 Claims, 10 Drawing Sheets

METHOD AND DEVICE FOR SCOREKEEPING WATCH

RELATED APPLICATIONS

This application claims priority from U.S. provisional patent Ser. No. 61/314,174 filed Mar. 16, 2010 which is incorporated herein by reference.

FIELD OF THE INVENTION

The present invention generally relates to wrist watches and, more particularly, to wrist watches that provide scores to the user while the game of tennis is being played.

BACKGROUND OF THE INVENTION

Various types of watches have been described in the prior art, some of which are illustrated in the following publications:
  a. U.S. Pat. No. 7,773,461 of Crosby et al., discloses a score monitoring wrist watch specifically modified for tennis matches.
  b. U.S. Pat. No. 5,574,422 of Martin, that discloses a volleyball score monitoring device with speaker.
  c. U.S. Pat. No. 5,795,300 of Bryars, that discloses a pulse monitoring wrist watch.
  d. U.S. Patent Application 2003/0008733 of Allshouse et al., that discloses a tennis table with wireless scoring synchronization mechanism.
  e. U.S. Patent Application 2007/0032893 of Lowran, that discloses a tennis table with wireless scoring synchronization mechanism.

SUMMARY OF THE INVENTION

According to various embodiments of the invention a device for monitoring a first player is provided. The device is for monitoring a first player, and may include a location unit arranged to receive transmissions from multiple short-range transmitters at multiple points in time and to generate, based on the transmissions, location information about locations of the first player at the multiple points in time; a score button that once pressed by the first player provides a first player score indication; a score calculating unit arranged to: receive the first player score indication, transmit a first player score message to another device that is designed to trigger a first player score alert, determine whether to update a first player score value based on at least zero responses to the first player score message, and update the first player score value based on the determination; a feedback unit arranged to receive a second player score message about an intent of a second player to update a second player score value, generate a second player score alert, and transmit a first player response based on at least zero responses of the first player to the second player score alert; and a display for displaying the first player score value and at least one other player score value.

The feedback unit may be arranged to generate an audio second player score alert.

The feedback unit may be arranged to generate a video second player score alert.

The device may include another score button that once pressed by the first player provides the first player response.

The device may include a sensor unit for sensing physiological information about the player.

The device may include a processor arranged to process the physiological information and to detect physiological events.

The device may include a receiver for receiving short range transmissions of physiological information from a physiological sensor.

The device may include a communication manager arranged to establish an access protected communication with at least one other peer.

The communication manager may be arranged to participate in set up session during which short range communication set up messages are exchanged with peers that are proximate to the device.

The device may include an accelerometer.

The device may include short range receiver for receiving accelerometer information from an accelerometer located in a racket of the player.

The device may include a transmitter for transmitting the location information.

The device may include a controller that may be arranged to determine an operational mode of the device.

The device may include a controller that may be arranged to upload a player profile and to control device based on the player profile.

The device may include a controller that may be arranged to upload a game profile and to control device based on the game profile.

A device for monitoring a first player is provided. According to an embodiment of the invention device may include a communication manager arranged to establish an access protected communication with at least one other peer; a score button that once pressed by the first player provides a first player score indication; a score calculating unit arranged to: receive the first player score indication, transmit a first player score message to another device that is designed to trigger a first player score alert, determine whether to update a first player score value based on at least zero responses to the first player score message, and update the first player score value based on the determination; a feedback unit arranged to receive a second player score message about an intent of a second player to update a second player score value, generate a second player score alert, and transmit a first player response based on at least zero responses of the first player to the second player score alert; and a display for displaying the first player score value and at least one other player score value.

The device may include a location unit arranged to receive transmissions from multiple short-range transmitters at multiple points in time and to generate, based on the transmissions, location information about locations of the first player at the multiple points in time.

The feedback unit may be arranged to generate an audio second player score alert.

The feedback unit may be arranged to generate a video second player score alert.

The device may include another score button that once pressed by the first player provides the first player response.

The device may include a sensor unit for sensing physiological information about the player.

The device may include a processor arranged to process the physiological information and to detect physiological events.

The device may include a receiver for receiving short range transmissions of physiological information from a physiological sensor.

The device may include a communication manager arranged to establish an access protected communication with at least one other peer.

The communication manager may be arranged to participate in set up session during which short range communication set up messages are exchanged with peers that are proximate to the device.

The device may include an accelerometer, a gyroscope, a magnetometer or a combination of at least two of these elements.

The device may include a short range receiver for receiving accelerometer information from an accelerometer located in a racket of the player.

The device may include a transmitter for transmitting the location information.

The device may include a controller that may be arranged to determine an operational mode of the device.

The device may include a controller that may be arranged to upload a player profile and to control device based on the player profile.

The device may include a controller that may be arranged to upload a game profile and to control device based on the game profile.

BRIEF DESCRIPTION OF THE DRAWINGS

The present invention will be readily understood by the following detailed description in conjunction with the accompanying drawings, wherein like reference numerals designate like structural elements.

DETAILED DESCRIPTION OF THE DRAWINGS

The following figures illustrate exemplary embodiments of the invention. They are not intended to limit the scope of the invention but rather assist in understanding some of the embodiments of the invention. It is further noted that all the figures are out of scale.

A device is attached to a player (hereinafter referred to as a first player). The device can receive information from another device of another player (referred to as a second player). The phrases first and second are merely used to differentiate between the player sand have no other significance.

Figure 1:
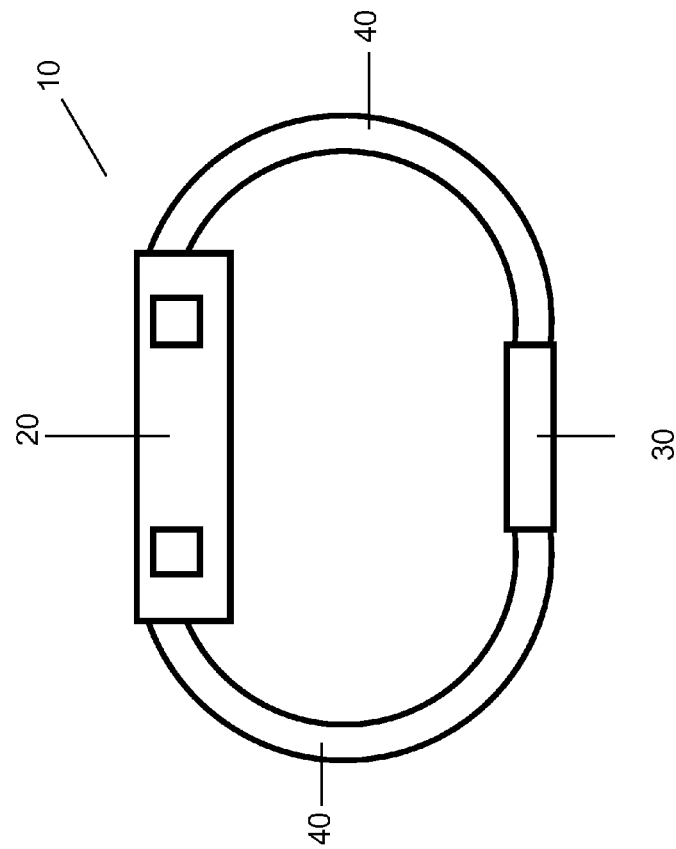
FIG. 1 is a side view of an device according to an embodiment of the invention.

FIG. 1 illustrates device 10 according to an embodiment of the invention.

The device 10 may be used for score keeping in variety of games, including but not limited to tennis, badminton, squash, volleyball, racquetball, table tennis, beach ball, or other suitable ball games. Consequently the present invention may appear in variety of configurations and shape factors. Conveniently we choose to describe the invention embodiment adapted for tennis.

The device 10 includes a control and monitor unit 20, a sensor unit 30 and may include a wrist belt 40 (or may be connected to such a wrist belt or other means for attaching the device to a player). The control and display unit 20 can operate in a plurality of modes, including a time monitor mode, health monitor mode, game score mode and some other relevant display modes.

The sensor unit 30, once the device 10 is worn by a player, may be located near the player's artery and may measure players pulse, heartbeat and some other physiological and biomechanical characteristics. The reading of the physiological signals of a player enables a detection of high heart-lung strain, calorie consumption, physical tonus changes during long games or any other suitable statistics.

In some embodiments the sensor unit 30 may be located on a different mount, for example a separate belt mounted on players' chest. In some embodiments, the sensor unit 30 may include motion and positioning sensors, including accelerometers and additionally or alternatively, gyroscopes.

The reading of the motion and positioning sensors enable detection of the game-related activities, including player's rest between sets, acceleration of the racket, players jumping and running, and other suitable events and their parameters.

The wrist belt 40 may be Velcro belt, or any other suitable wrist belt with a fastener unit. The control and monitor unit 20 may resemble a large conventional wrist watch and may have the same form factor. It may be worn as a wrist watch with band, or it may be worn as a pendant watch, or a clip-on, or like a necklace, chain, or rope style.

Figure 2:
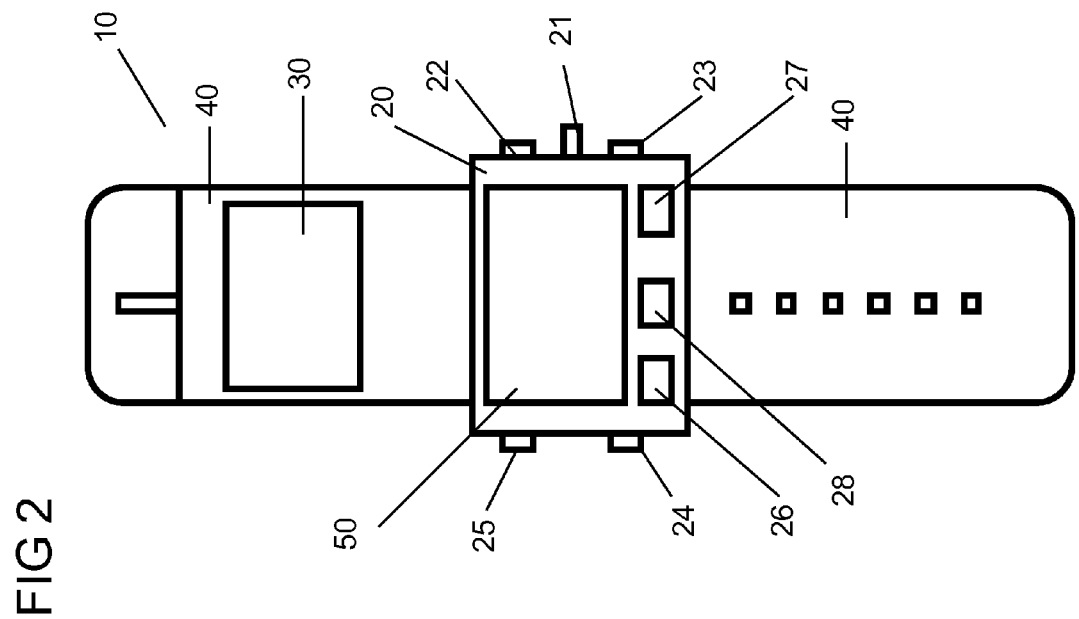
FIG. 2 is a top view of an device according to an embodiment of the invention.

FIG. 2 is a top view of the device 10. The control and monitor unit 20 is illustrated as including an liquid crystal device (LCD) LCD display 50 and plurality of buttons 21, 22, 23, 24, 25, 26, 27 and 28.

Back light control button 21 controls the backlight. When pressed it activates backlight LEDs and enables accurate reading of the LCD display 50 even in a dark environment.

Menu button 22 can activate context-sensitive menu which enables the player to set his/hers profile, choose display mode, modify settings and perform multiple additional activities.

Setting button 23 can be used to toggle, on each menu screen, between viewing and editing mode, in which the player modifies the screen.

Pulse button 24, once pressed can cause the display 50 to display physiological information to the player, such as pulse rate, breath rate, and a number of calories burnt during the game. This button (or any other button) can be pressed and in response a menu will be displayed. The menu can allow to select between signals from different sensors, can be used to adjust sensors and the like. The se sensors can include pulse sensors, location unit, accelerometer, gyroscope and magnometer.

Timer button 25 can activate or stop a time and may cause the device 10 to operate in a timer mode, in which the device calculates the time between subsequent presses. The watch may be further configured to sound an audible alarm given time after the start button has been pressed.

Score button 26 can allow a player to suggest a change in the score of the first player. It can also provide page-down functionality in the menu of the watch.

Pressing score button 26, when the device 10 is in a scorekeeping mode, may result in changing (at least provisionally) the first player score. Each device can count by itself various events such as mistakes or scoring events, by pressing buttons 26 and/or 27. If, buttons 26 and 27 are used to count scores than another button (such as 28) can be used for counting errors.

It is noted that the device 10 can have multiple buttons for affecting the score of the first player. For example, FIG. 2 illustrates an additional score button 27.

The additional score button 27 can also affect the score value but in a manner that differs from the affect of score button 26. For example—one score button may be used to increase the score value while the other is used to decrease the score value. Yet for another example—one score button may be used to increase a point while another is aimed to increase a set or match value.

The additional score button 27 may provide page-up functionality in the menu of the watch. Pressing the additional score button 27, when the device 10 is in a scorekeeping mode, may results on decreasing of the player's score.

Approval button 28 (WIN/OK) acts as an approval (OK) of the menu screen.

Pressing the approval button 28 in scorekeeping mode signals player's victory in a given set and beginning of a new set.

Figure 3:
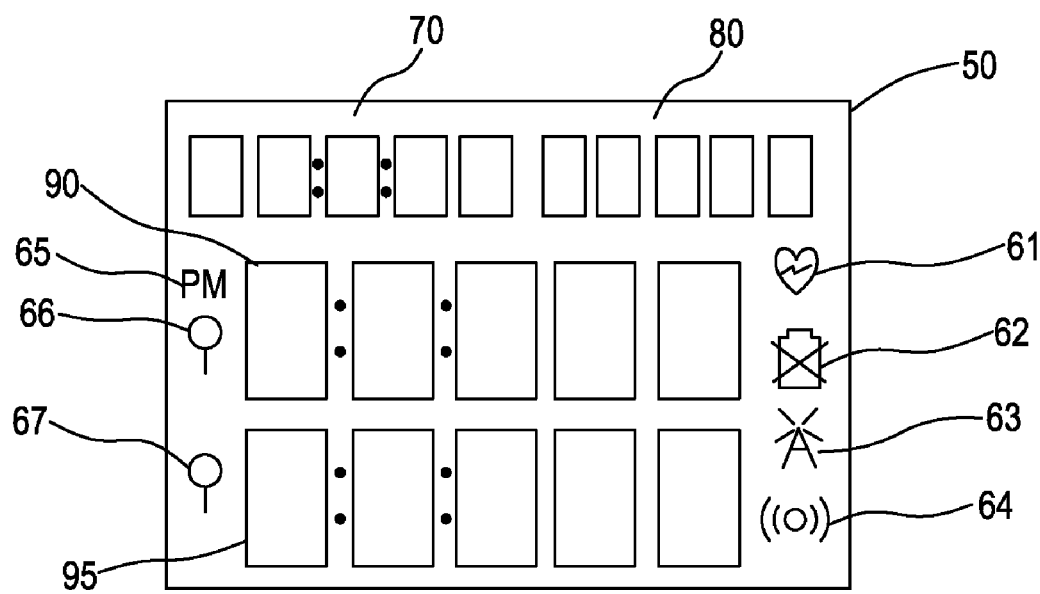
FIG. 3 illustrates a display unit of the device according to an embodiment of the invention.

FIG. 3 illustrates a display 50 that may be configured to show plurality of status indicators and information lines.

Each indicator event may be accompanied by a specific sound from the watch's speaker.

Heartbeat indicator 61 may light up when the physiological sensors indicate dangerous physical strain, including high pulse, high blood pressure and other suitable events.

Battery status indicator 62 may light up when the battery of the wrist watch is low.

Wireless status indicator 63 can light up when the wrist watch looses communication with another wrist watch.

Volume indicator 64 shows the volume of the wrist watch speaker.

AM/PM indicator 65 provides a time AM/PM indicator.

Ambient temperature indicator 66 shows ambient temperature.

Humidity indicator 67 shows atmospheric humidity.

If the heat strain, measured by temperature and humidity, becomes too high for the match to continue, the device 10 may sound an audible alarm.

The date and counter line 70 displays the current date in the timekeeping mode and the runtime and errors counter in the current set in scorekeeping mode.

The status line 80 displays the day of the week in timekeeping mode and player status in scorekeeping mode.

The player score line 90 displays the time in timekeeping mode and the first player score, when in scorekeeping mode.

The second player score line 95 displays the time in timekeeping mode and the second player score in scorekeeping mode.

It is noted that in a multi-player game the score can reflect the score of the team that includes a player.

Figure 4:
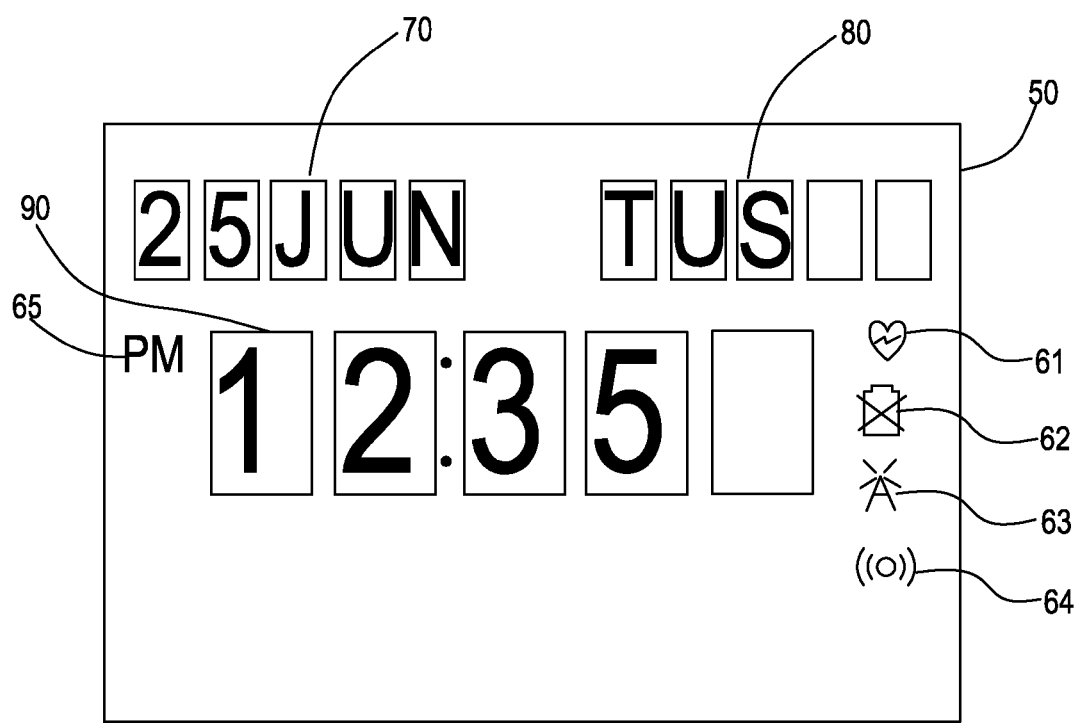
FIG. 4 illustrates displayed content when the device is in a timekeeping mode according to an embodiment of the invention.

FIG. 4 illustrates a display user screen example in timekeeping mode of the present invention. The display is configured to display a specific time: Tuesday 25 June, 12:35 pm. The timer is not set, and therefore the timer line 95 is not displayed.

Figure 5:
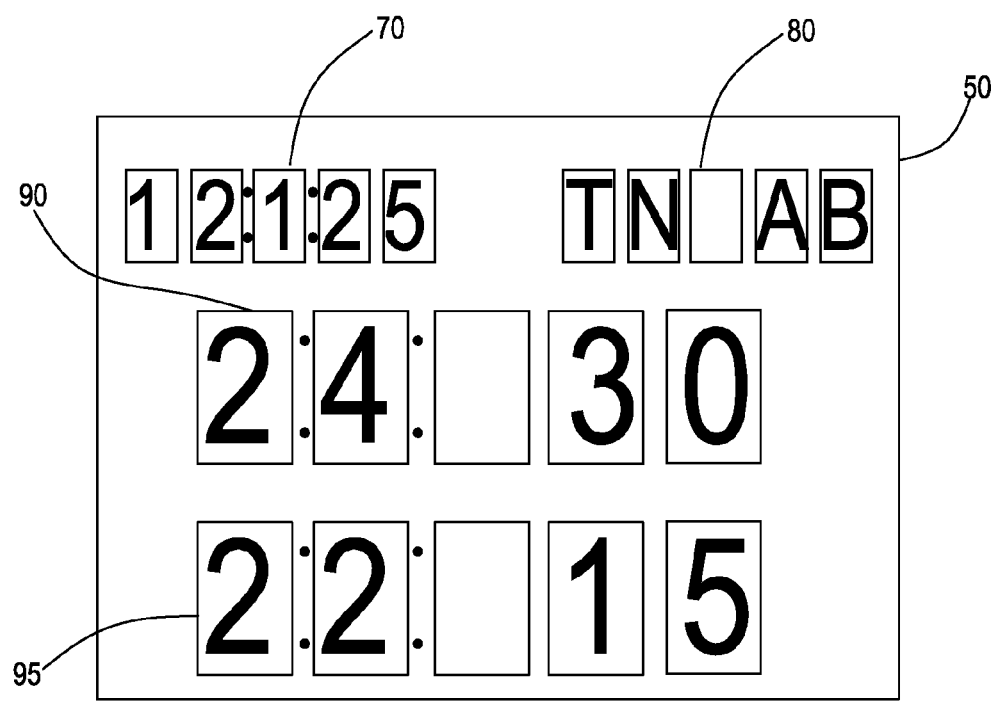
FIG. 5 illustrates displayed content when the device is in a scorekeeping mode according to an embodiment of the invention.

FIG. 5 illustrates a display user screen example in scorekeeping mode of the present invention.

The date and counter line 70 is configured to display the number of the errors the player made (12) and the runtime of the current set (1:30).

The status line 80 is configured to display the players status.

The first two letters indicate the game being played, where TN stands for tennis.

The third letter indicates the player authorization. This can be useful in a multi-player team game in which the player is a part of a team. By default, the player may modify the score for his team. If a player is defined as a viewer, he/she cannot modify the score. If the player is defined as referee, he/she can modify the scores for both teams. The last two digits indicate the currently serving team. The first team and the second team score lines 90 and 95 indicate the current score, including the results of previous games (2:2), the results in current game (2:4) and the results of the current set (15:30). Since the scorekeeping screen contains many informative fields, the user may choose not to display the indicators in the scorekeeping mode.

Figure 6:
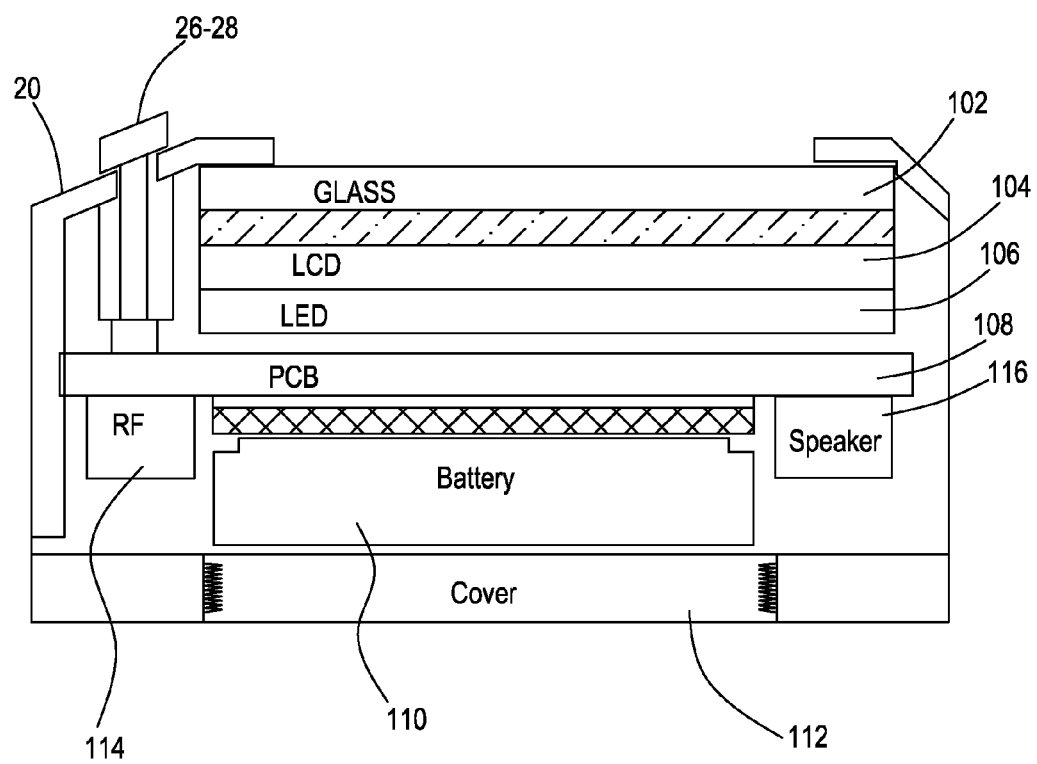
FIG. 6 illustrates a cross section of the device according to an embodiment of the invention.

FIG. 6 illustrates a control and monitor unit hardware design for the present invention. The control and monitor unit 20 includes several hardware components. The buttons 26-28 are mounted upon the control and monitor unit 20. The LCD display screen 50 is constructed from glass layer 102, LCD layer 104 and backlight LED layer 106. The microprocessor, memory and other suitable components are integrated on a PCB 108 positioned under the LCD. The battery 110 is positioned further under the PCB 108. The battery is conveniently closed by the battery cover 112. The RF component 114 enables communication between the wrist watches. The speaker component 116 sound audible signal upon qualifying events.

Figure 7:
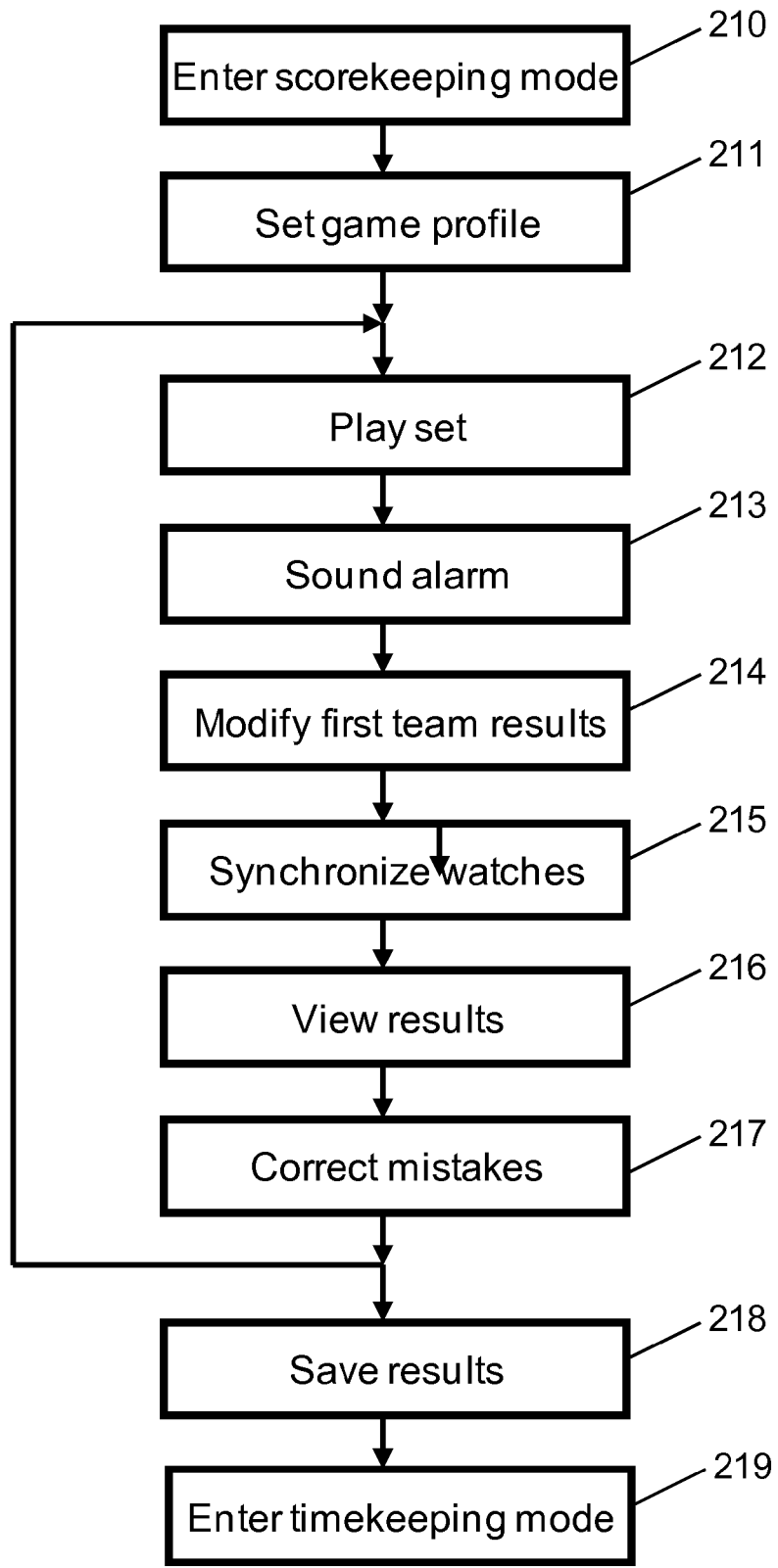
FIG. 7 illustrates a method according to an embodiment of the invention.

FIG. 7 illustrates a method for setting the score results of the present invention.

Before the beginning of the game the player enters scorekeeping mode 210. The player sets the profile of the game 211, including user name, type of the game, ability to modify scores, maximal length for each set, the role of the user in the team, and various other suitable parameters. If the game is continued from a previous store point, it is sufficient to load previously defined setting.

In each set the player performs variety of operations. After pressing start button 25, the player plays the game 212 until an event happens. If one of the teams scores enough points for win, the player presses the button 28. If no team scored enough points during the predefined time period, the wrist watch sounds an alarm 213. The alarm may also sound 213 if a player reaches dangerous physiological measures.

Figure 8:
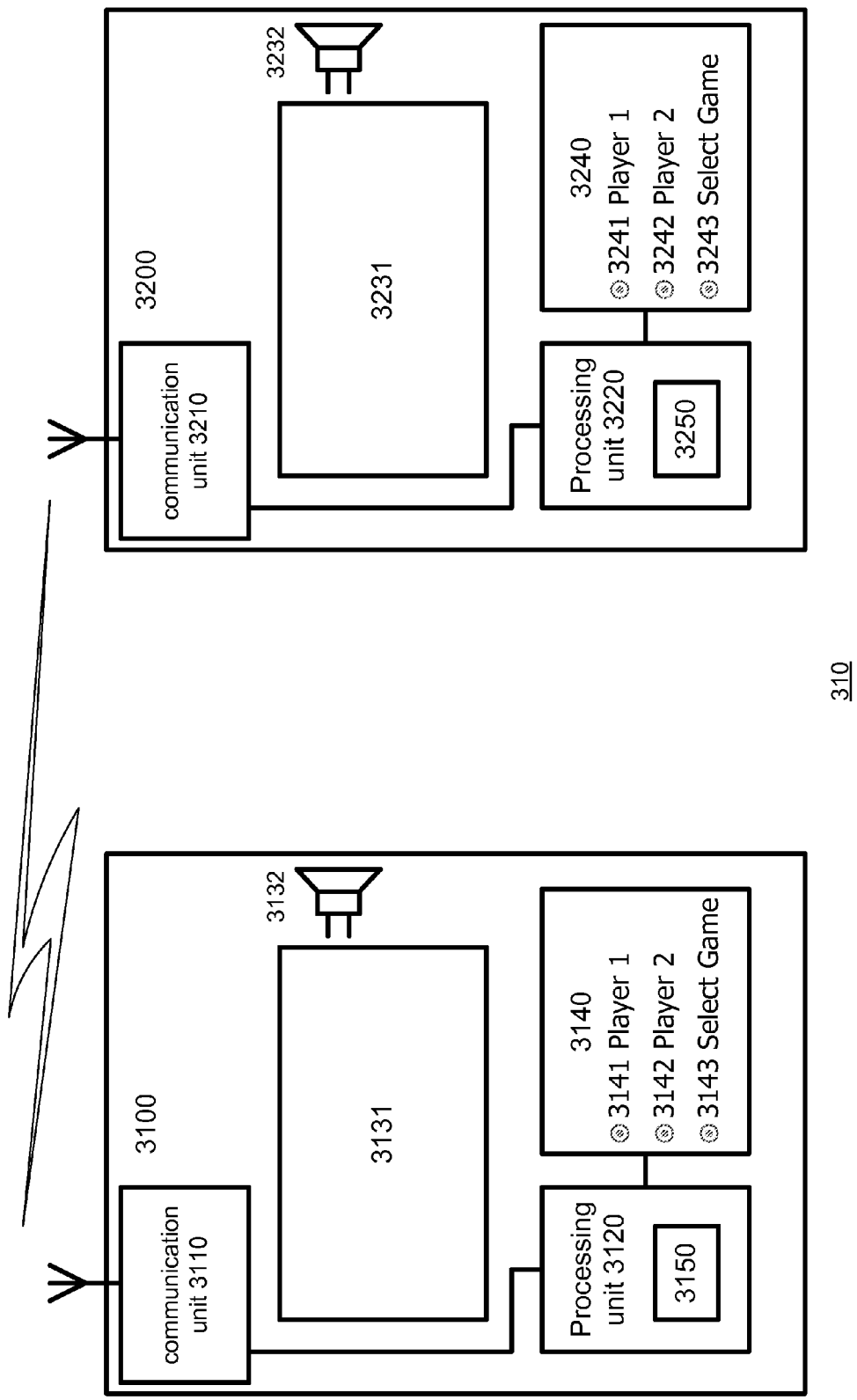
FIG. 8 illustrates two devices according to an embodiment of the invention.

Upon the alarm, a player of the winning team presses the victory button 26. The result is the synchronized between the watches 215, so that all players see the same result. The system may be adapted so that only one player in each team or a referee can upgrade score for each game. An error still may occur. Upon update of the game results, the players should view their watches 216. In case of an error, the players may undo the latest score entries by pressing button 27. At this point the players may continue to play the game 212. After winning the game, the player may press button 28 and save the results of the game 218 for future analysis or to continue the game on another occasion. After finishing the game, the player may enter the watch into timekeeping mode 219 and use it as any other wrist watch FIG. 8 illustrates system 310, according to an embodiment of the invention. System 310 includes first device 3100 and second device 3200, each of which includes a communication unit (denoted 3110 and 3210 respectively), and at least one output component (such as a display 3131 or 3231 respectively, and/or or a speaker 3132 or 3232 respectively). Additionally, each of the first and second devices 3100 and 3200 includes a processing unit (denoted 3120 and 3220, respectively) which is configured to determine a game related score in response to an input that is received either from an input interface (denoted 3140 or 3240 respectively) or from the communication unit 3110 or 3210 of the user device 3100 or 3200.

The processing unit 3120 (3220) either includes or can otherwise access a games rules module 3150 (3250), that includes rules for the determination of game related scoring of at least one game. Input interface 3140 (3240) usually includes at least two buttons (or other type of interface) denoted 3141, 3142, 3241, 3242, that enables a user to indicate which of the players won a sub-game (e.g. a game round). Other buttons (e.g. 3143, 3243) may enable a user to select a type of game (e.g. ping-pong, basketball, tennis, volleyball, racketlon and the like).

Conveniently, each of devices 3100 and 3200 is a small or miniature device, which can be hold by a player, be applied on a player hand or other part of the body, connected to a clothing of the player, and so forth. Each device has processor and memory for support and execute various rules of different games, provide user with visible and audio information According to an embodiment of the invention, at least one of devices 3100 and 3200 is able to adopt/install other kind of information such as personal data to modify existing rules or new rules for new games.

It is noted that communication units 3110 (3210) enable a wireless connection between the device (which may, according to an embodiment of the invention, be interface by additional device, such optional 3rd device serving players as central transmitting station in case when distance between players is greater that communication range of devices 3100 and 3220).

Conveniently, each of the devices 3100 and 3200 includes dedicated software, for operating processing units 3120 (3220).

It is noted that, according to an embodiment of the invention, one of the devices (e.g. first device 3100) may act as a master device, while the other device (e.g. second device 3200) may act as a slave device. Those roles may be, according to an embodiment of the invention, selected by a user, by the devices, and/or interchanged.

Figure 9:
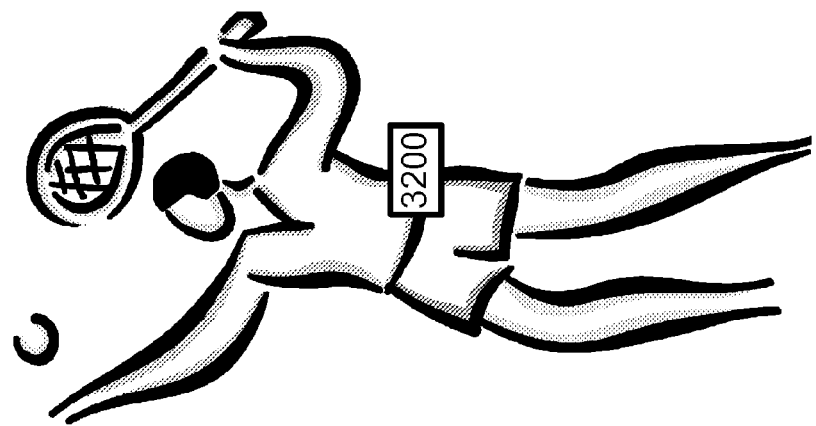
FIG. 9 illustrates two players and devices according to an embodiment of the invention.
Figure 9:
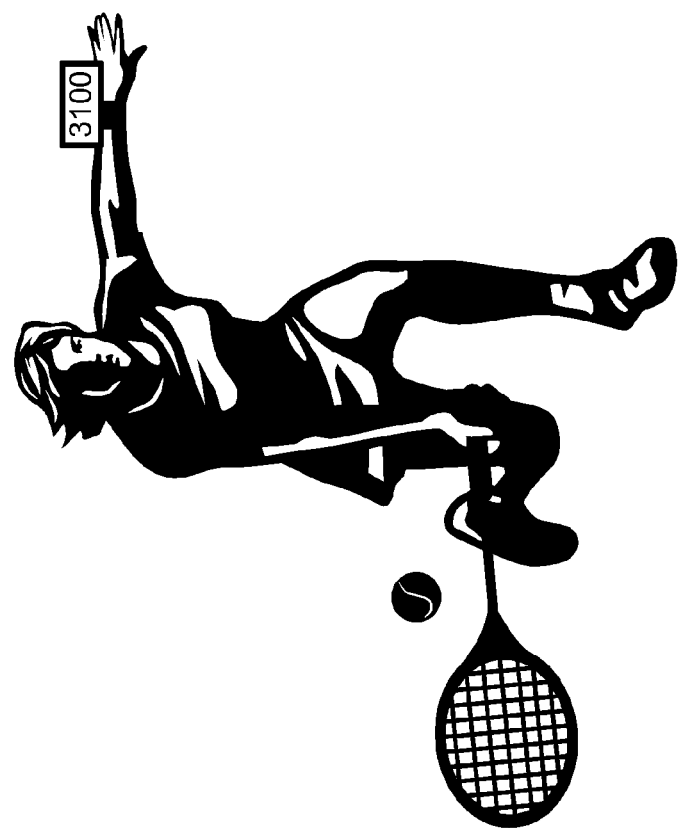

FIG. 9 illustrates devices 3100 and 3200 that are worn by two players, according to an embodiment of the invention.

It is noted that, according to an embodiment of the invention, system 310 may include more than two devices, depending upon the type of the game.

A method for using system 310 is further disclosed, according to an embodiment of the invention.

The method starts with activating both of the devices.

The activation is conveniently followed by a selection of a game type out of multiple game type (usually by at least one user, wherein the selection of the game type is usually preceded by displaying on at least one of the devices a list of preloaded games)

The method further includes, according to an embodiment of the invention, a stage of selecting a master device of the two devices.

It is noted that the selection of the master device, if carried out, may take place either before of after the selection of the game type, according to different embodiments of the invention. According to an embodiment of the invention, the selection of master is made by the first device of the two to be initiated. The selected one of the devices is initiated by pressing start button.

Upon selecting, the second device is operating in the "slave" mode which means it cannot overrule decision of first device.

When the method continues, each time when sub-play is finished, the master device receives an identity of the winner and/or number of points won by one or more of the players. E.g. the "name" of winner may be activated on the first device by pressing one out of two appropriated button, or by otherwise inputting such information.

According to an embodiment of the invention, the method includes (and the aforementioned devices are configured to support) indicating by one or more of the devices that a break point in the game was reached, wherein such point is determined by the processing unit of one or more of the devices. E.g. Once players achieve break point when service should pass to the second player, first device providing visual and/or audio signal and pass to the "slave" mode while the second device become master" device.

The game continues until reaching a next break point according to the game rules will be achieved [1st logical loop].

The game continues until reaching a finish point according to the game rules will be achieved [2nd logical loop].

The method usually further includes determining, by a processing unit of at least one of the device, that the game was finished, which is usually followed by displaying information regarding a scoring of the game. E.g. at this moment both devices providing visual and audio signal reflecting final results of the game [score of the last game, winner of the last game, total score, history, etc.]

The method can be implemented by one or more non-transitory computer readable media, having computer readable code embodied therein, which includes instruction that when carried out by one or more processors, implement the method.

Figure 10:
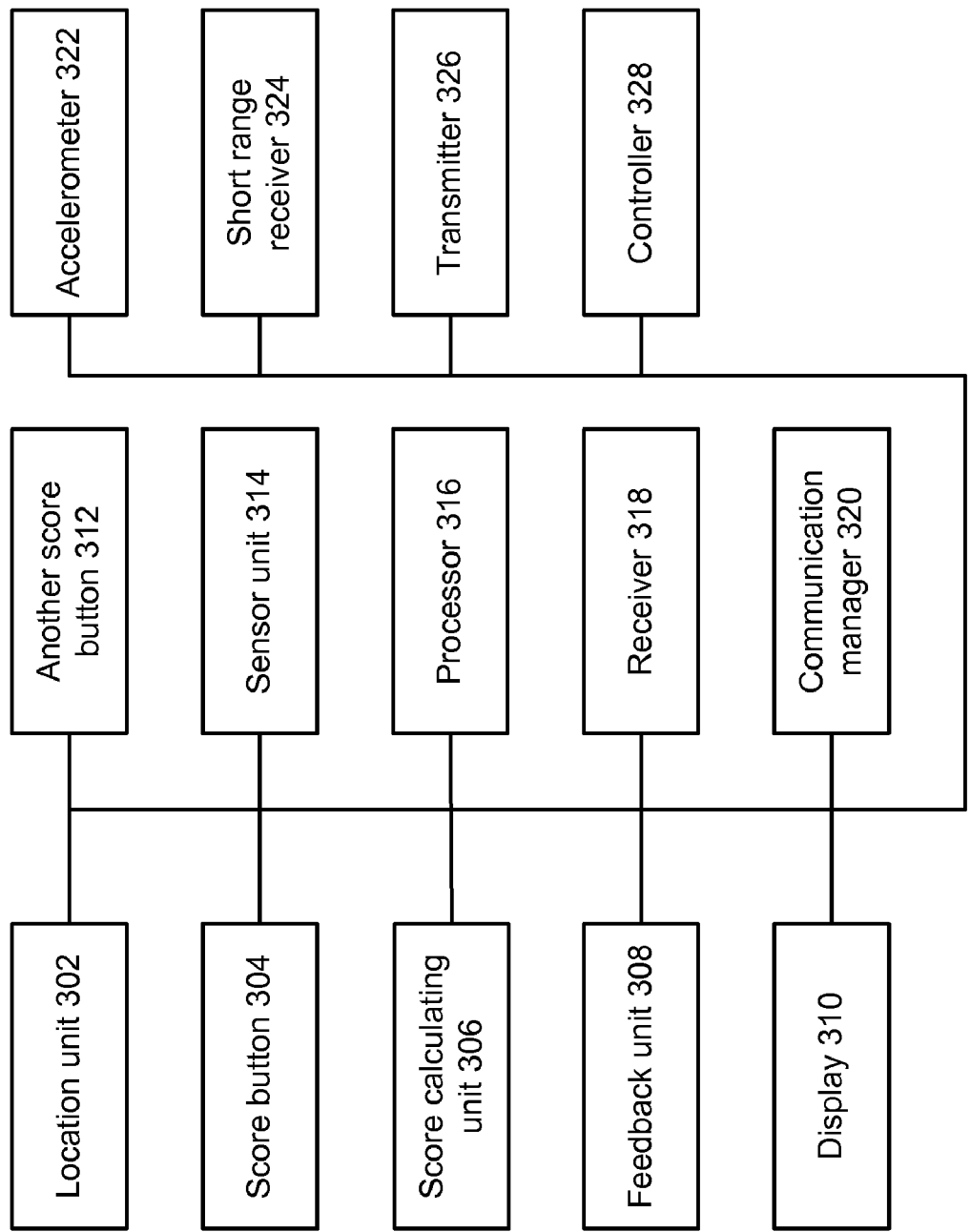
FIG. 10 illustrates a device according to an embodiment of the invention.

FIG. 10 illustrates a device 300 according to an embodiment of the invention.

FIG. 10 illustrates device 300 as including various units or modules. It is noted that according to various embodiments of the invention the device 300 may include only some of the illustrated units or modules. For example, according to an embodiment of the invention the device 300 may include a location unit 302, a score button 304, a score calculating unit 306, a feedback unit 308 and a display and zero or more additional units or modules. Yet for another example, the device 300 may include a communication manager 320, a score button 304, a score calculating unit 306, a feedback unit 308 and a display and zero or more additional units or modules.

Device 300 may include: (i) location unit 302 arranged to receive transmissions from multiple short-range transmitters at multiple points in time and to generate, based on the transmissions, location information about locations of the first player at the multiple points in time; (ii) a score button 304 that once pressed by the first player provides a first player score indication; (iii) a score calculating unit 306 that is arranged to: receive the first player score indication, transmit a first player score message to another device that is designed to trigger a first player score alert, determine whether to update a first player score value based on at least zero responses to the first player score message, and update the first player score value based on the determination; (iv) a feedback unit 308 arranged to receive a second player score message about an intent of a second player to update a second player score value, generate a second player score alert, and transmit a first player response based on at least zero responses of the first player to the second player score alert; and (v) a display 310 for displaying the first player score value and at least one other player score value.

The feedback unit 308 may be arranged to generate an audio second player score alert.

The feedback unit 308 may be arranged to generate a video second player score alert. It may be displayed on display 310.

The device 300 may include another score button 312 that once pressed by the first player provides the first player response.

The device 300 may include a sensor unit 314 for sensing physiological information about the player.

The device 300 may include a processor 316 arranged to process the physiological information and to detect physiological events.

The device 300 may include a receiver 318 for receiving short range transmissions of physiological information from a physiological sensor.

The device 300 may include a communication manager 320 arranged to establish an access protected communication with at least one other peer.

The communication manager 320 may be arranged to participate in set up session during which short range communication set up messages are exchanged with peers that are proximate to the device.

The device 300 may include an accelerometer 322.

The device 300 may include short range receiver 324 for receiving accelerometer information from an accelerometer located in a racket of the player.

The device 300 may include a transmitter 326 for transmitting the location information.

The device 300 may include a controller 328 that may be arranged to determine an operational mode of the device.

The controller 328 may be arranged to upload a player profile and to control device based on the player profile.

The controller 328 may be arranged to upload a game profile and to control device based on the game profile.

The device 300 may be attached to a user in various manners including by a belt, an elastic strip and the like. It can be shaped like any of the previously described devices—including the device of FIGS. 1 and 2.

Figure 11:
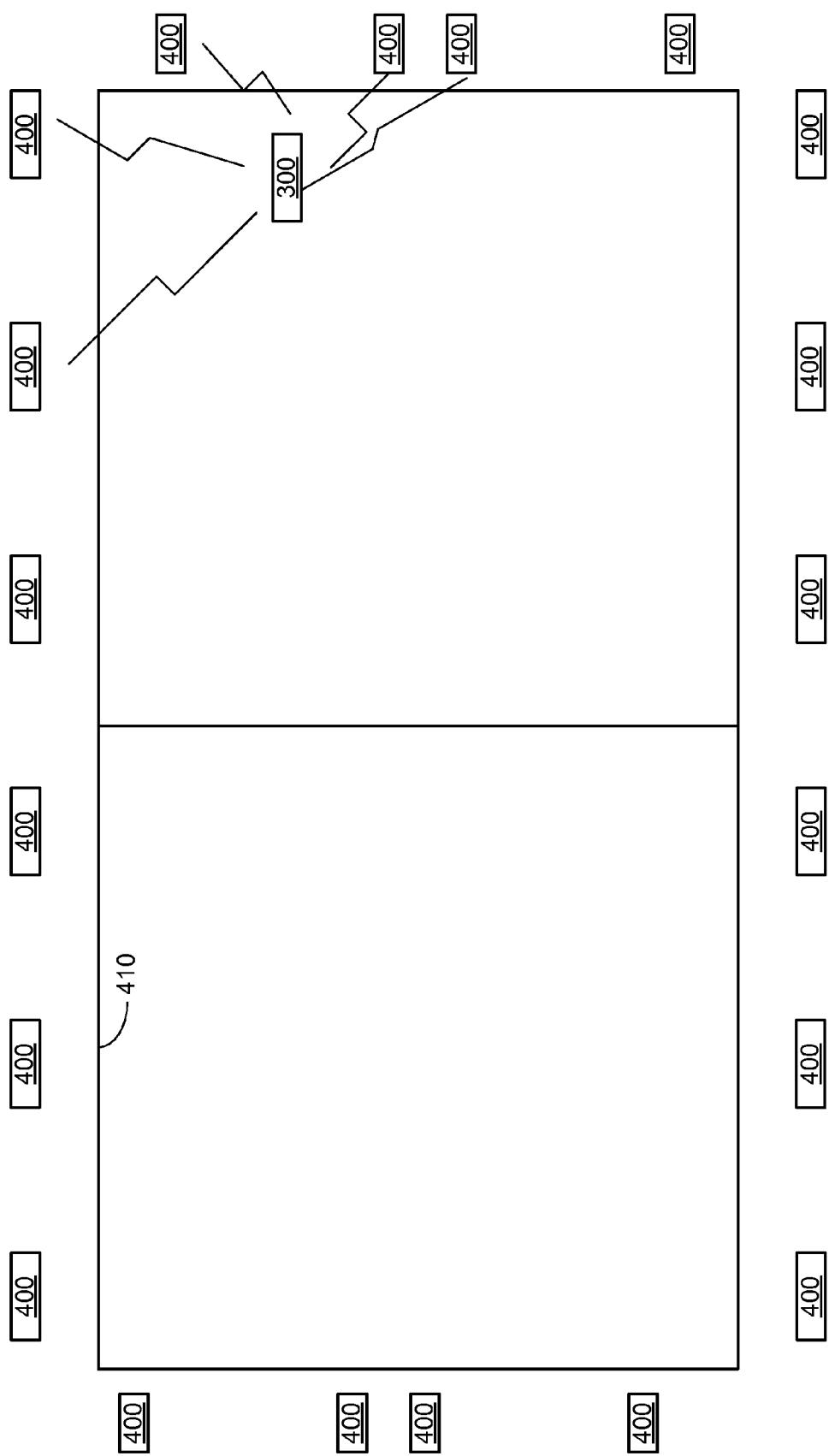
FIG. 11 illustrates a device and its environment according to an embodiment of the invention.

FIG. 11 illustrates device 300 and its environment according to an embodiment of the invention.

Device 300 is worn by a player that plays tennis. The tennis court 410 is surrounded with a group of short range transmitters 400. At any point on the tennis court the location unit 302 of device 300 receives transmissions from at least one short-range transmitter of the group 400. The location unit 302 can calculate the location of the player based on the received short range transmissions by using triangulation or any prior art location algorithm. A very short-range transmitter can have its own identifier and the location unit 302 can receive the identifier and determine the location of the player. The identifier can be a data field or may be a transmission parameter such as frequency, modulation, timing of transmission and the like. The location of the player can be monitored at multiple points in time and be stored and even processed in order to evaluate the player's game or practice.

The player can also be monitored by a video camera. FIG. 11 illustrates that the device 300 receives the short range transmissions of few short-range transmitters that are proximate to the device 300—although it may receive (Depending upon the transmission parameters of the short range transmitters and the reception parameters of the device) transmissions from more distant short-range transmitters 400. It may also receive fewer short-range transmissions.

According to an embodiment of the invention any of the mentioned above devices can include accelerometer, a gyroscope, a magnetometer or a combination of at least two of these elements.

If the device includes more than a single sensor (for example—a sensor out of a physiological sensor, an accelerometer, a location unit, a gyroscope, a magnetometer) then information from these sensors (or at least some) can be correlated or otherwise compared to each other to provide better and more accurate on a player, a player movement, and the like. It is noted that information from other sensors (camera) can be also correlated with information of one of these sensors.

The player can be monitored and the monitoring information can be stored and processed and used for various purposes such as scouting.

It is to be understood that the architectures depicted herein are merely exemplary, and that in fact many other architectures can be implemented which achieve the same functionality. In an abstract, but still definite sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality.

Furthermore, those skilled in the art will recognize that boundaries between the functionality of the above described operations merely illustrative. The functionality of multiple operations may be combined into a single operation, and/or the functionality of a single operation may be distributed in additional operations. Moreover, alternative embodiments may include multiple instances of a particular operation, and the order of operations may be altered in various other embodiments.

However, other modifications, variations and alternatives are also possible. The specifications and drawings are, accordingly, to be regarded in an illustrative rather than in a restrictive sense.

Unless stated otherwise, terms such as "first" and "second" are used to arbitrarily distinguish between the elements such terms describe. Thus, these terms are not necessarily intended to indicate temporal or other prioritization of such elements.

I claim:

1. A device for monitoring a first player, the device comprises:
   a location unit arranged to receive transmissions from multiple short-range transmitters at multiple points in time and to generate, based on the transmissions, location information about locations of the first player at the multiple points in time;
   a score button that once pressed by the first player provides a first player score indication;
   a score calculating unit arranged to:
     receive the first player score indication,
     transmit a first player score message to another device that is designed to trigger a first player score alert,
     determine whether to update a first player score value based on at least zero responses to the first player score message, and
     update the first player score value based on the determination;

a feedback unit arranged to receive a second player score message about an intent of a second player to update a second player score value, generate a second player score alert, and transmit a first player response based on at least zero responses of the first player to the second player score alert; and a display for displaying the first player score value and at least one other player score value.

2. The device according to claim 1, wherein the feedback unit is arranged to generate an audio second player score alert.

3. The device according to claim 1, wherein the feedback unit is arranged to generate a video second player score alert.

4. The device according to claim 1, comprising another score button that once pressed by the first player provides the first player response.

5. The device according to claim 1, comprising a sensor unit for sensing physiological information about the player.

6. The device according to claim 5, comprising a processor arranged to process the physiological information and to detect physiological events.

7. The device according to claim 1, comprising a receiver for receiving short range transmissions of physiological information from a physiological sensor.

8. The device according to claim 1, comprising a communication manager arranged to establish an access protected communication with at least one other peer.

9. The device according to claim 8, wherein the communication manager is arranged to participate in set up session during which short range communication set up messages are exchanged with peers that are proximate to the device.

10. The device according to claim 1, comprising an accelerometer.

11. The device according to claim 1, comprising a short range receiver for receiving accelerometer information from an accelerometer located in a racket of the player.

12. The device according to claim 1, comprising a transmitter for transmitting the location information.

13. A device for monitoring a first player, the device comprises:

a communication manager arranged to establish an access protected communication with at least one other peer;

a score button that once pressed by the first player provides a first player score indication;

a score calculating unit arranged to:
receive the first player score indication,
transmit a first player score message to another device that is designed to trigger a first player score alert,
determine whether to update a first player score value based on at least zero responses to the first player score message, and
update the first player score value based on the determination;

a feedback unit arranged to receive a second player score message about an intent of a second player to update a second player score value, generate a second player score alert, and transmit a first player response based on at least zero responses of the first player to the second player score alert; and a display for displaying the first player score value and at least one other player score value.

14. The device according to claim 13, comprising a location unit arranged to receive transmissions from multiple short-range transmitters at multiple points in time and to generate, based on the transmissions, location information about locations of the first player at the multiple points in time.

15. The device according to claim 13, comprising another score button that once pressed by the first player provides the first player response.

16. The device according to claim 13, comprising a sensor unit for sensing physiological information about the player.

17. The device according to claim 13, comprising a receiver for receiving short range transmissions of physiological information from a physiological sensor.

18. The device according to claim 13, comprising an accelerometer.

19. The device according to claim 13, comprising a short range receiver for receiving accelerometer information from an accelerometer located in a racket of the player.

20. The device according to claim 13, comprising a controller that is arranged to upload a player profile and to control device based on the player profile.

21. The device according to claim 13, comprising a controller that is arranged to upload a game profile and to control device based on the game profile.

22. The device according to claim 13, comprising a controller that is arranged to determine an operational mode of the device.

* * * * *